(12) United States Patent
Goldberg et al.

(10) Patent No.: US 9,809,631 B2
(45) Date of Patent: *Nov. 7, 2017

(54) TARGETING OF PODOPLANIN WITH LECTIN FOR USE IN THE PREVENTION AND TREATMENT OF CANCER

(71) Applicant: Rowan University, Glassboro, NJ (US)

(72) Inventors: Gary S. Goldberg, Glassboro, NJ (US); Yongquan Shen, Glassboro, NJ (US)

(*) Notice: Subject to any disclaimer, the term of this patent is extended or adjusted under 35 U.S.C. 154(b) by 24 days.

This patent is subject to a terminal disclaimer.

(21) Appl. No.: 14/921,641

(22) Filed: Oct. 23, 2015

(65) Prior Publication Data

US 2016/0207968 A1 Jul. 21, 2016

Related U.S. Application Data

(63) Continuation of application No. 13/218,717, filed on Aug. 26, 2011, now Pat. No. 9,169,327, which is a continuation-in-part of application No. 12/401,849, filed on Mar. 11, 2009, now Pat. No. 8,114,593.

(60) Provisional application No. 61/069,198, filed on Mar. 12, 2008, provisional application No. 61/085,039, filed on Jul. 31, 2008.

(51) Int. Cl.
| | |
|---|---|
| *C07K 14/42* | (2006.01) |
| *A61K 38/17* | (2006.01) |
| *A61K 9/00* | (2006.01) |
| *C07K 16/28* | (2006.01) |
| *C07K 16/30* | (2006.01) |
| *C12Q 1/68* | (2006.01) |
| *G01N 33/574* | (2006.01) |
| *A61K 39/00* | (2006.01) |

(52) U.S. Cl.
CPC ............ *C07K 14/42* (2013.01); *A61K 9/0053* (2013.01); *A61K 38/178* (2013.01); *C07K 16/28* (2013.01); *C07K 16/3046* (2013.01); *C12Q 1/6886* (2013.01); *G01N 33/57484* (2013.01); *A61K 2039/505* (2013.01); *C07K 2317/73* (2013.01); *C07K 2319/30* (2013.01); *C07K 2319/60* (2013.01); *C12Q 2600/136* (2013.01); *C12Q 2600/158* (2013.01); *C12Q 2600/178* (2013.01); *G01N 2333/47* (2013.01)

(58) Field of Classification Search
None
See application file for complete search history.

(56) References Cited

U.S. PATENT DOCUMENTS

| | | | | |
|---|---|---|---|---|
| 7,527,802 B2 * | 5/2009 | Glenn | ................. | A61K 9/0019 424/184.1 |
| 2005/0176933 A1 * | 8/2005 | Chen | .................... | C07K 16/303 530/388.8 |
| 2009/0232814 A1 * | 9/2009 | Goldberg | ........... | C07K 16/3046 424/138.1 |

OTHER PUBLICATIONS de Mejía et al. (Critical Reviews in Food Science and Nutrition, 45: 425-445, 2005).*
Bornhorst et al. (Methods Enzymol., 326: 245-254, 2000).*

* cited by examiner

*Primary Examiner* — Brad Duffy
*Assistant Examiner* — Nelson B Moseley, II
(74) *Attorney, Agent, or Firm* — Fox Rothschild LLP

(57) ABSTRACT

Lectin compositions and methods for reducing tumor cell growth and preventing or treating cancer are provided.

24 Claims, 1 Drawing Sheet

SEQUENCE LISTING

<160> NUMBER OF SEQ ID NOS: 23

<210> SEQ ID NO 1
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1
tgcatcctgc accaccaact                                              20

<210> SEQ ID NO 2
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 2
tgcctgcttc accacttc                                                19

<210> SEQ ID NO 3
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 3
catggcgtga tttcatatgc gcga                                         24

<210> SEQ ID NO 4
<211> LENGTH: 24
<212> TYPE: DNA
<213> ORGANISM: Artificial sequence
<220> FEATURE:
<223> OTHER INFORMATION: Synthetic oligonucleotide

```
<400> SEQUENCE: 4
tccagaagaa gatgttggcg acct                                          24

<210> SEQ ID NO 5
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 5
accgagctgc aagaactctt cctc                                          24

<210> SEQ ID NO 6
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 6
aggaggcctt ccatctgttg ct                                            22

<210> SEQ ID NO 7
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 7
accaacacag acgaccaaga cact                                          24

<210> SEQ ID NO 8
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 8
aagcatccac tgtgccttca gttc                                          24

<210> SEQ ID NO 9
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 9
gagaagttcg actgtcacta ctgc                                          24

<210> SEQ ID NO 10
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 10
ctgatcctgg taagtgattc ctcc                                          24

<210> SEQ ID NO 11
<211> LENGTH: 24
```

```
<212> TYPE: DNA
<213> ORGANISM: Artificial sequence
<220> FEATURE:
<223> OTHER INFORMATION: Synthetic oligonucleotide

<400> SEQUENCE: 11
tgttctcaga gcccagcatc actt                                              24

<210> SEQ ID NO 12
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 12
acatcctctc agctggttcc ttca                                              24

<210> SEQ ID NO 13
<211> LENGTH: 29
<212> TYPE: DNA
<213> ORGANISM: Artificial sequence
<220> FEATURE:
<223> OTHER INFORMATION: Synthetic oligonucleotide

<400> SEQUENCE: 13
ctgtgaaccg cataagagaa tcaaggagg                                         29

<210> SEQ ID NO 14
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 14
tgcctcgagt agtacttggc ttgt                                              24

<210> SEQ ID NO 15
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 15
atagagtctg tcatcatggg ctgg                                              24

<210> SEQ ID NO 16
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 16
acaggcttcc tgtcaagcag aga                                               23

<210> SEQ ID NO 17
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 17
```
aacatcccag agcctttgac tcct                                    24

<210> SEQ ID NO 18
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 18
caaagctgcc atagctctat tcgg                                    24

<210> SEQ ID NO 19
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 19
aagccaggac tctcacatgc aact                                    24

<210> SEQ ID NO 20
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 20
agctttgcag atggaacgga acac                                    24

<210> SEQ ID NO 21
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 21
tggatggcat ctcagtaggg agcta                                   25

<210> SEQ ID NO 22
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 22
ttgcacacca gtcccatgca aa                                      22

<210> SEQ ID NO 23
<211> LENGTH: 249
<212> TYPE: PRT
<213> ORGANISM: Maackia amurensis

<400> SEQUENCE: 23

Ser Asp Glu Leu Ser Phe Thr Ile Asn Asn Phe Val Pro Asn Glu Ala
 1               5                  10                  15

Asp Leu Leu Phe Gln Gly Glu Ala Ser Val Ser Ser Thr Gly Val Leu
            20                  25                  30

Gln Leu Thr Arg Val Glu Asn Gly Gln Pro Gln Gln Tyr Ser Val Gly
        35                  40                  45

-continued

| | | | | | | | | | | | | |
|---|---|---|---|---|---|---|---|---|---|---|---|---|
| Arg | Ala | Leu | Tyr | Ala | Ala | Pro | Val | Arg | Ile | Trp | Asp | Asn | Thr | Thr | Gly |
| | 50 | | | | | 55 | | | | 60 | | | | | |
| Ser | Val | Ala | Ser | Phe | Ser | Thr | Ser | Phe | Thr | Phe | Val | Val | Lys | Ala | Pro |
| 65 | | | | | 70 | | | | | 75 | | | | | 80 |
| Asn | Pro | Thr | Ile | Thr | Ser | Asp | Gly | Leu | Ala | Phe | Phe | Leu | Ala | Pro | Pro |
| | | | | 85 | | | | | 90 | | | | | 95 | |
| Asp | Ser | Gln | Ile | Pro | Ser | Gly | Arg | Val | Ser | Lys | Tyr | Leu | Gly | Leu | Phe |
| | | | | 100 | | | | | 105 | | | | | 110 | |
| Asn | Asn | Ser | Asn | Ser | Asp | Ser | Ser | Asn | Gln | Ile | Val | Ala | Val | Glu | Phe |
| | | | 115 | | | | | 120 | | | | | 125 | | |
| Asp | Thr | Tyr | Phe | Gly | His | Ser | Tyr | Asp | Pro | Trp | Asp | Pro | Asn | Tyr | Arg |
| | | 130 | | | | | 135 | | | | | 140 | | | |
| His | Ile | Gly | Ile | Asp | Val | Asn | Gly | Ile | Glu | Ser | Ile | Lys | Thr | Val | Gln |
| 145 | | | | | 150 | | | | | 155 | | | | | 160 |
| Trp | Asp | Trp | Ile | Asn | Gly | Gly | Val | Ala | Phe | Ala | Thr | Ile | Thr | Tyr | Leu |
| | | | | 165 | | | | | 170 | | | | | 175 | |
| Ala | Pro | Asn | Lys | Thr | Leu | Ile | Ala | Ser | Leu | Val | Tyr | Pro | Ser | Asn | Gln |
| | | | 180 | | | | | 185 | | | | | 190 | | |
| Thr | Ser | Phe | Ile | Val | Ala | Ala | Ser | Val | Asp | Leu | Lys | Glu | Ile | Leu | Pro |
| | | 195 | | | | | 200 | | | | | 205 | | | |
| Glu | Trp | Val | Arg | Val | Gly | Phe | Ser | Ala | Ala | Thr | Gly | Tyr | Pro | Thr | Gln |
| | 210 | | | | | 215 | | | | | 220 | | | | |
| Val | Glu | Thr | His | Asp | Val | Leu | Ser | Trp | Ser | Phe | Thr | Ser | Thr | Leu | Glu |
| 225 | | | | 230 | | | | | 235 | | | | | 240 | |
| Ala | Asn | Cys | Asp | Ala | Ala | Thr | Glu | Asn | | | | | | | |
| | | | 245 | | | | | | | | | | | | |

US 9,809,631 B2

TARGETING OF PODOPLANIN WITH LECTIN FOR USE IN THE PREVENTION AND TREATMENT OF CANCER

INTRODUCTION

This application is a continuation-in-part application of U.S. patent application Ser. No. 12/401,849, filed Mar. 11, 2009, which claims benefit of priority from U.S. Provisional Patent Application Ser. Nos. 61/069,198, filed Mar. 12, 2008, and 61/085,039, filed Jul. 31, 2008, the contents of each of which are incorporated herein by reference in their entirety.

This invention was made with government support under grant number CA88805-01A2 and R01CA126897 awarded by the National Institutes of Health. The government has certain rights in the invention.

BACKGROUND OF THE INVENTION

Progress in methods to detect and treat cancer has led to increased five-year survival rates. However, cancer mortality rates have not decreased proportionately (Welch, et al. (2000) *JAMA* 283:2975-2978). Some transformed cells can survive medical treatment and lay dormant for years before they emerge to cause relapse in a patient. Nontransformed cells can force tumor cells to assume a normal morphology and phenotype by a process called "Contact Normalization" (Glick & Yuspa (2005) *Semin. Cancer Biol.* 15:75-83; Rubin (2003) *Adv. Cancer Res.* 90:1-62).

Increased anchorage-independent growth and migration distinguish cancer cells from their nontransformed precursors (Frisch & Screaton (2001) *Curr. Opin. Cell Biol.* 13:555-562; Giancotti & Buoslahti (1999) *Science* 285:1028-1032). Src kinase, a membrane-bound tyrosine kinase, phosphorylates Cas (Crk associated substrate) to promote these fundamental hallmarks of tumor cell growth (Brabek, et al. (2004) *Oncogene* 23:7406-7415; Cho & Klemke (2000) *J. Cell Biol.* 149:223-236; Goldberg, et al. (2003) *J. Biol. Chem.* 278:46533-46540; Honda, et al. (1998) *Nat. Genet.* 19:361-365; Huang, et al. (2002) *J. Biol. Chem.* 277:27265-27272; Klemke, et al. (1998) *J. Cell Biol.* 140:961-972; Shin, et al. (2004) J. Biol. Chem. 279:38331-38337).

Src has been implicated in many human cancers (Frame (2002) *Biochim. Biophys. Acta* 1602:114-130; Irby & Yeatman (2000) *Oncogene* 19:5636-5642). Increased Src activity has been reported in cancers of the colon (Cartwright, et al. (1994) *J. Clin. Invest* 93:509-515; Cartwright, et al. (1989) *J. Clin. Invest* 83:2025-2033; Cartwright, et al. (1990) Proc. Natl. Acad. Sci. USA 87:558-562), and particularly in metastatic colon cancer that invades liver (Termuhlen, et al. (1993) *J. Surg. Res.* 54:293-298). Increased Src activity is also found in cancers of the pancreas (Lutz, et al. (1998) *Biochem. Biophys. Res. Commun.* 243:503-508), lung (Mazurenko, et al. (1992) *Eur. J. Cancer* 28:372-377); neural cells (Bjelfman, et al. (1990) *Mol. Cell Biol.* 10:361-370; Bolen, et al. (1985) *Proc. Natl. Acad. Sci. USA* 82:7275-7279), muscle (Rosen, et al. (1986) J. Biol. Chem. 261:13754-13759), ovaries (Budde, et al. (1994) *Cancer Biochem. Biophys.* 14:171-175; Wiener, et al. (1999) *Clin. Cancer Res.* 5:2164-2170), esophagus (Kumble, et al. (1997) *Gastroenterology* 112:348-356), skin (Bjorge, et al. (1996) *Biochem. Cell Biol.* 74:477-484; Munshi, et al. (2000) *J. Immunol.* 164:1169-1174), stomach (Takeshima, et al. (1991) *Jpn. J. Cancer Res.* 82:1428-1435), and breast (Ottenhoff-Kalff, et al. (1992) *Cancer Res.* 52:4773-4778; Rosen, et al. (1986) supra; Verbeek, et al. (1996) *J. Pathol.* 180:383-388). Indeed, metastatic cell growth can be reduced by agents that inhibit Src activity (Lutz, et al. (1998) supra; Roginskaya, et al. (1999) *Leukemia* 13:855-861; Staley, et al. (1997) *Cell Growth Differ.* 8:269-274).

Cas is an important component of the focal adhesion complex signaling network (Bouton, et al. (2001) *Oncogene* 20:6448-6458) that also includes FAK, Grb2, Shc, and paxillin (Schlaepfer, et al. (1999) *Prog. Biophys. Mol. Biol.* 71:435-478; Sieg, et al. (1999) *J. Cell Sci.* 112 (Pt 16):2677-2691). After phosphorylation by Src, Cas an bind to other proteins including Crk, PI-3-kinase, Nc, and PLCy (Burnham, et al. (1996) *Oncogene* 12:2467-2472; Sakai, et al. (1994) *EMBO J.* 13:3748-3756; Vuori, et al. (1996) *Mol. Cell Biol.* 16:2606-2613). Src transformation of homozygous null Cas knockout (CasKO) cells does not fully promote their anchorage-independence or ability to migrate. These transformed growth characteristics can be conferred to CasKO cells by transfection with wild-type Cas (Brabek, et al. (2005) Mol. Cancer Res. 3:307-315; Goldberg, et al. (2003) supra; Honda, et al. (1998) supra; Huang, et al. (2002) supra).

Src phosphosphorylates Cas to inhibit Fhl1 expression thereby promoting nonanchored cell growth and migration (Shen, et al. (2006) *Cancer Res.* 66:1543-1552). Fhll is composed of four and half LIM domains and can move between intercellular junctions (Huang, et al. (2002) *Yi. Chuan Xue. Bao.* 29:953-958), focal adhesions, and the nucleus (Brown, et al. (1999) *J. Biol. Chem.* 274:27083-27091) to affect gene expression (Qin, et al. (2005) *FEBS Lett.* 579:1220-1226; Taniguchi, et al. (1998) *Mol. Cell Biol.* 18:644-654). Transfection studies demonstrate that Fh11 specifically blocks nonanchored tumor cell growth and migration, but does not affect "normal" anchored cell growth (Shen, et al. (2006) supra). Therefore, Fhll acts as a true tumor suppressor rather than as a general mitotic inhibitor. Analysis of human clinical specimens suggests that Fhll expression is suppressed in some human tumors including those of breast, kidney, and prostate. Furthermore, Fhll expression is suppressed by Src, and is restored during Contact Normalization of transformed cells (Shen, et al. (2006) supra). Thus, Fhll acts downstream of Src and Cas to suppress the anchorage-independence and motility that leads to metastatic cell growth.

Lectin, which is a protein selectively binding to carbohydrates, has originally been discovered from plants, microorganisms, virus, invertebrates or vertebrates and widely used as a material for various disease-related researches. Lectin has various functions: it has been known to agglutinate erythrocytes to sediment them, and has been used in determining blood type. In addition, it has been shown to have a function of specifically agglutinating cancer cells and lectins from Korean legume *Maackia fauriei* and Korean marine crab *Philyra pisum* have been shown to exhibit anti-proliferative activity (U.S. Pat. No. 7,045,300 and U.S. Pat. No. 7,015,313).

SUMMARY OF THE INVENTION

The present invention features methods for preventing or reducing tumor cell growth and migration, reducing tumor size and vascularization and preventing or treating cancer with an isolated lectin that binds sialic acid. In some embodiments, the lectin is administered orally. In other embodiments, the lectin is a plant lectin from *Maackia amurensis, Trichosanthes japonica, Viscum album, Artocarpus intergrifolia,* or *Sambucus nigra*. In particular embodiments the lectin has the sequence set forth in SEQ ID NO:23. Pharmaceutical compositions and kits are also provided.

DETAILED DESCRIPTION OF THE INVENTION

Figure 1:
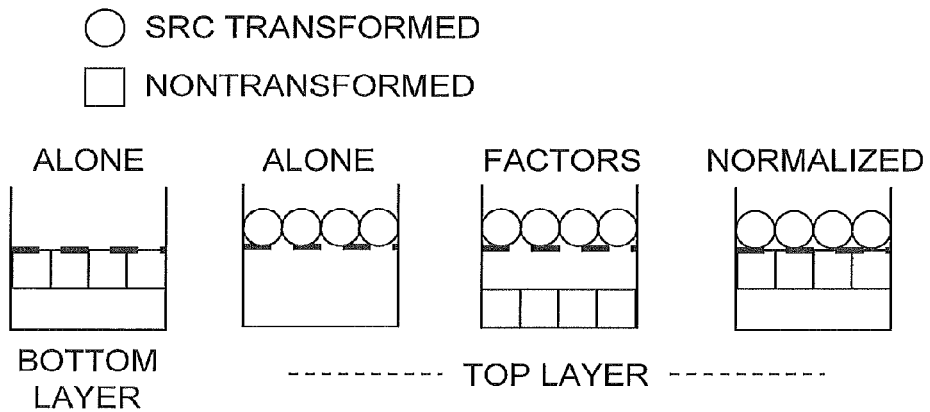
FIG. 1 depicts a layered culture system. Nontransformed or Src transformed Cx43Ko cells were incubated beneath or on top of a porous membrane that prevents actual mixing of the cell populations. Transformed cells separated by 1 mm from nontransformed cells enabled communication by diffusible factors but not intercellular junctions. Transformed cells incubated directly over nontransformed cells allowed for intercellular junctional communication and Contact Normalization.

A comprehensive analysis has now been performed to identify genes that are modulated during Contact Normalization. Contact normalization describes the ability of nontransformed cells (i.e., normal cells) to normalize the growth of neighboring transformed or cancer cells. Tumor cells need to overcome this form of growth inhibition before they can become malignant or metastatic. The analysis herein identified specific genes which were activated in transformed cells, but suppressed in nontransformed cells. Moreover, the expression of these genes was inhibited in transformed cells that were undergoing Contact Normalization. In addition, genes whose expression was decreased in transformed cells, but increased by Contact Normalization were also identified. Thus, these genes serve as viable biomarkers and chemotherapeutic targets in the diagnosis, prognosis and treatment of cancer. Indeed, analysis of one particular biomarker, Podoplanin (Pdpn; GENBANK Accession Nos. NP_001006625, NP_001006626, NP_006465, and NP_938203), indicated that targeting this unique transmembrane receptor with a lectin that binds sialic acid, inhibits transformed cell growth and migration in vitro. In particular, it was shown that *M. amurensis* lectin inhibits cell migration prior to inhibiting cell viability. For example, 308 nM MAA suppresses melanoma cell migration by over 99%, while inhibiting cell viability by about 20% within the same time period. In addition, dietary administration of lectin inhibited subcutaneous melanoma growth and vascularization in mice. This analysis demonstrated that lectins can be used to target Pdpn to attack cancer cells.

Accordingly, the present invention provides the use of a lectin that binds sialic acid on Pdpn in methods for preventing or reducing tumor cell growth and migration, reducing tumor size and vascularization and preventing or treating cancer. In some embodiments, the lectin is isolated and optionally purified. As used herein, a protein is said to be "isolated" when physical, mechanical or chemical methods are employed to remove the protein from cellular constituents that are normally associated with the protein. A skilled artisan can readily employ standard purification methods to obtain an isolated protein. A purified lectin molecule will be substantially free of other proteins or molecules and is generally 95% to 100% homogenous. The nature and degree of isolation and purification will depend on the intended use.

The lectin of the present invention can be isolated and optionally purified using conventional methods. For example, when isolated from its natural source, the lectin can be purified to homogeneity on appropriate immobilized carbohydrate matrices and eluted by proper haptens. See, Goldstein & Poretz (1986) In *The lectins. Properties, functions and applications in biology and medicine* (ed. Liener et al.), pp. 33-247. Academic Press, Orlando, Fla.; Rudiger (1993) In *Glycosciences: Status and perspectives* (ed. Gabius & Gabius), pp. 415-438. Chapman and Hall, Weinheim, Germany. Alternatively, the lectin can be produced by recombinant methods according to established methods. See Streicher & Sharon (2003) *Methods Enzymol.* 363:47-77. As yet another alternative, lectins can be generated using standard peptide synthesis technology or using chemical cleavage methods well-known in the art based on the amino acid sequences of known lectins or the lectin disclosed herein.

The lectin can also be modified in a way to form a chimeric molecule containing lectin fused to another, heterologous polypeptide or amino acid sequence. In one embodiment, such a chimeric molecule is a fusion of the lectin with a polyhistidine epitope tag, which provides an epitope to which immobilized nickel can selectively bind. The epitope tag is generally placed at the amino- or carboxyl-terminus of a protein. In an alternative embodiment, the chimeric molecule can include a fusion of the lectin with an immunoglobulin or a particular region of an immunoglobulin.

Lectins of particular use in the instant invention are those that bind sialic acid. Examples of such lectins include those listed in Table 1.

TABLE 1

| Organism | Species or Cell Type | Lectin | Binding Specificity |
|---|---|---|---|
| Virus | Sendai virus | HN | NeuAcα2, 3Galpβ1, 3GalNac/4GlcNAc |
|  | Human parainfluenza virus type 1 | HN | NeuAcα2, 3Galβ1, 4GlcNac |
| Bacteria | *Streptococcus mitis* | SABP | Neu5Acα2, 3Galβ1, 3GalNac |
|  | *Mycoplasma pneumoniae* | HA-A | Neu5Acα2, 3Galβ1, 4GloNAcP 1,3 |
| Fungi | *Polyporus squamosus* | PSA | Neu5Acα2, 6Galβ1, 4Glc/Glc NAc |
|  | *Psathyrella vetutina* | PVS | Neu5Acα2, 6Galβ1, 4GlcNAc |
|  | *Macrophomina phaseolina* | MPL | Neu5Acα2, 3Galβ1, 4GlcNAc |
| Plants | *Maackia amurensis* | MAL | Neu5Acα2, 3Galβ1, 4GlcNAc |
|  |  | MAH | Neu5Acα2, 3Galβ1, 3 [Neu5Ac a2, 6] GalNAc |
|  | *Trichosanthes japonica* | TJA | Neu5Acα2, 6Galβ1, 4GlcNAc |
|  | *Viscum album* | ML-1 | Neu5Acα2, 6Galβ1, 4GlcNAc |
|  | *Artocarpus intergrifolia* | jacalin | Gal and Man > Neu5Ac |
|  | *Sambucus nigra* | SNA | Neu5Acα2, −6Gal (NAc) -R |
| Insects | *Allomyrina dichotoma* | Allo A-II | Neu5Acα2, 6Galβ1, 4GlcNAc |
| Animals | blood macrophages | IL-lα Siglec-1 | Neu5Acα2, 3Galβ1, 4GlcNAc Neu5Acα, 3Gal |

For example, the *M. amurensis* lectins are composed of two types of lectin molecules (MAH and MAL), which display slightly different binding preferences. It has been shown that this mixture can specifically suppress anchorage-independence and motility of Src transformed cells at nM concentrations. Analysis of MAH and MAL separately can determine if either of these compounds is more effective at preventing malignant cell growth than the mixture found in nature.

As shown in Table 1, sialic acid (N-acetylneuraminic acid; Neu5Ac or NANA) binding lectins can be derived from virus, bacterial, fungal, plant, insect, and animal sources. For example, analysis herein indicates that jacalin, which preferentially associates with glycoconjugates containing galactosyl (β1,3)N-acetylgalactosamine, may actually augment tumor cell migration. In contrast, MAH or MAL, which preferentially associate with 0-glycosidically linked oligosaccharides having galactosyl (β1,4)N-acetylglucosamine structures with (α2,3) linked sialic acid, can prevent nonanchored tumor cell growth and migration. Taken together, this analysis indicates that specific lectins can associate with Pdpn and suppress nonanchored cell growth and migration required for tumor cell invasion and progression. In this respect, lectins such as MPL from *M. phaseolina* and TJA from *T. japonica* can be analyzed for similar binding specificities. These compounds can be obtained from a variety of sources including Sigma-Aldrich, Calbiochem, and Vector Laboratories. In particular embodiments, the lectin used in accordance with the present invention is that set forth in SEQ ID NO:23.

Fluorescence microscopy can be used to determine if specific lectins colocalize with Pdpn. Moreover, immunoprecipitation can be used to determine if Pdpn and lectins associate with each other. To determine if lectins that bind to Pdpn can suppress nonanchored growth and migration of Src transformed cells, Src transformed cells and nontransformed cells are treated with various concentrations of specific lectins that bind to Pdpn, as well other lectins with different binding affinities (see, e.g., Table 1). Mouse embryonic fibroblasts, and other established cell lines, including LA25 cells, can be used for these experiments. The effects of several concentrations of specific lectins on the anchored growth, nonanchored growth, and migration of Src transformed and nontransformed cells are quantitated. It is expected that specific lectins will inhibit the malignant growth potential of tumor cells at concentration that will not inhibit the "normal" growth of nontransformed cells. This is demonstrated by showing that specific lectins significantly inhibit nonanchored growth and migration of transformed cells, without significantly interfering with the anchored growth of parental nontransformed control cells.

For use in vitro or an experimental setting, e.g., to identify synergistic therapies in a cell-based or animal model system, a tumor cell is contacted with a lectin that binds sialic acid so that tumor cell growth and migration is measurably decreased, reduced or inhibited, e.g., by 25%, 50%, or 75% as compared to a tumor cell not contacted with the lectin. The term "contacted" when applied to a cell is used herein to describe the process by which a lectin is delivered to a target cell or is placed in direct proximity with the target cell. This delivery may be in vitro or in vivo and may involve the use of a recombinant vector system. Any method may be used to contact a cell with lectin, so long as the method results in either increased levels of lectin at the tumor cell. This includes both the direct delivery of lectin to the cell and the delivery of a gene or DNA segment that encodes the lectin.

Lectins that bind to sialic acid can also be used in therapeutic approaches for the prevention or treatment of cancers including malignant and metastatic cancers in subjects with cancer, subjects at risk of developing cancer or subjects harboring cancer cells affected by Contact Normalization. For therapeutic applications, the lectin is administered, e.g., in a pharmaceutically acceptable carrier and/or appropriate delivery vehicle, to reduce tumor size and vascularization and/or treat cancer. As used herein, the term "tumor" means a mass of transformed cells that are characterized, at least in part, by containing angiogenic vasculature. Although a tumor generally is a malignant tumor, i.e., a cancer having the ability to metastasize, a tumor also can be nonmalignant, provided that neovascularization is associated with the tumor. In some embodiments, tumor cells contemplated herein are derived from metastatic tumors. As used herein, the term "metastasis" refers to a secondary tumor that grows separately from the primary and has arisen from detached, transported cells.

The methods described herein are contemplated for use in the prevention or treatment of cancer and the incidence of tumor metastasis for all forms of tumors and cancer. Exemplary forms of cancer contemplated herein for treatment include head and neck squamous cell carcinoma, colon carcinoma, renal cancer, lung adenocarcinoma, human gastric cancer, breast cancer, cancer of the central nervous system, pancreatic cancer, liver cancer, ovarian cancer, prostate cancer, leukemia, skin cancer and the like. In particular embodiments, lectin is used in the treatment of a mammary carcinoma or melanoma.

As shown in the Examples, an effective amount of lectin inhibited transformed cancerous cells from proliferating and migrating and from forming a tumor in vivo. In view of the results disclosed herein, the skilled artisan would recognize that an effective amount of a particular lectin can vary depending on several factors, including the activity of the lectin, other components, if any, present in a pharmacologically acceptable composition containing the lectin, and the physico-chemical properties of the lectin. In accordance with the present invention, an "effective amount" of lectin is an amount that binds to Pdpn in a subject and inhibits tumor cell proliferation, vascularization and/or migration. In particular embodiments, treatment with a lectin disclosed herein provides at least a 25, 50, or 75% in tumor size as well as a measurable decrease in vascularization. In this respect, therapeutic use of the instant lectins can include the additional step of determining whether the tumor cells of the subject (e.g., cells of a biopsy sample) will bind lectin via Pdpn prior to administration and/or whether the lectin binds to Pdpn after administration.

As used herein, a "subject" means a mammal, including, for example, a human, a monkey or a cat, and the like. Subjects benefiting from therapeutic treatment with lectin include subjects wherein cancer has already been identified or has started progressing or metastasizing. Subjects benefiting from prophylactic treatment with lectin include subjects with a predisposition or increased risk of cancer (e.g., because of genetics or exposure to carcinogens), wherein cancer has not yet formed, established, progressed or metastasized.

An effective amount of lectin is preferably within the range of about 0.01 to about 500 mg/kg body weight, and can be readily determined by considering the activity of the particular lectin being administered, the route of administration, the period over which the lectin is to be administered, and other factors known to those skilled in the art. Thus, the lectins described herein can be used as medicaments for the treatment of a variety of cancer pathologies by inhibiting tumor cell growth and metastasis.

The in vivo effect of a therapeutic composition may be evaluated in a suitable animal model. For example, xenogenic cancer models wherein human cancer explants or passaged xenograft tissues are introduced into immune compromised animals, such as nude or SCID mice, are appropriate in relation to cancer and have been described (Klein, et al. (1997) Nature Medicine 3:402-408). For example, WO 98/16628 describes various xenograft models of human prostate cancer capable of recapitulating the development of primary tumors, micrometastasis, and the formation of osteoblastic metastases characteristic of late stage disease. Efficacy may be predicted using assays that measure inhibition of tumor formation, tumor regression or metastasis, and the like.

The lectin preparation, together with conventional additives, carriers or diluting agents, can be used to prepare pharmaceutical compositions, including individual doses thereof, in the form of tablets, filled capsules, or fluids such as solutions, mixtures, emulsions, elixirs or capsules filled with such, all for oral intake, as well as in the form of suppositories. Such pharmaceutical compositions and individual doses thereof can include conventional ingredients or principles, and such dosage-forms can contain any effective concentration of the active ingredients in accordance with the intended daily dosage range. Preparations that contain approximately 100, 200 or 300 mg of the lectin per individual dosage unit are representative of an appropriate concentration. However, dosages and administration protocols for the treatment of cancers using the foregoing methods may vary with the method and the target cancer and will generally depend on a number of other factors appreciated in the art.

The pharmaceutical composition according to the invention can be administered in a wide range of dosage-forms. Carriers used to produce a pharmaceutical containing the instant lectin can include both solid and liquid substances. Solid dosage-forms may include powders, tablets, pills, capsules, suppositories, or dispersible granules. A solid carrier can be one or more substances that function as a diluting agent, flavor additive, solvent, lubricant, suspension agent, binder, preservative, tablet-disintegrating substance or encapsulating material.

In powdered form, the carrier is a finely pulverized solid including lactose, hydroxypropylmethylcellulose and PVP, mixed with an appropriate amount of finely pulverized lectin preparation.

Appropriate carriers for powder and tablet forms include magnesium carbonate, magnesium stearate, talc, sugar, lactose, pectin, dextrin, stiffeners, gelatins, tragacanth, methylcellulose, and sodium carboxymethylcellulose. The term "composition" is meant to include dosage-forms where the active ingredients are enclosed in an encapsulating material whether or not associated with a carrier, including capsules or lozenges.

Suppositories are produced by melting a low-melting point wax and distributing the lectin therein. The melted, homogeneous mixture is then poured into forms and allowed to cool.

Compositions appropriate for vaginal administration can be presented as presses, tampons, creams, gels, pastes, foams or sprays that include, in addition to the active ingredient, suitable carriers known in the art.

Compositions in liquid form include solutions, suspensions, and emulsions, for example aqueous or propylene glycol solutions, together with coloring agents, flavor additives, stabilizing agents or diluting agents as appropriate. Also included are compositions in solid form that are meant to be converted to liquid form shortly prior to consumption. These forms may include, in addition to the active ingredients, artificial colors, flavors, stabilizers, buffers, natural or artificial sweeteners, dispersing agents, thickeners, dissolving agents and the like.

For topical administration to the epidermis, the lectin composition can be presented in the form of salves, creams, gels, skin washes or transdermal plasters. Salves and creams can be formulated with an aqueous or oil base, with the addition of suitable thickeners and/or gels. Skin washes can be prepared with an aqueous or oil base and may contain one or more emulsifying agents, stabilizers, dispersing agents, thickeners or fragrances.

Compositions suitable for topical administration in the mouth include lozenges that include active ingredients in an inert, flavored base, such as sucrose and Arabica gum, as well as mouth washes containing the active ingredients in a liquid carrier.

Solutions or mixtures may be administered directly to the nasal cavity using conventional means, such as drops or sprays. The composition may be produced in individual or multi-dose forms. Multi-dose forms would include a dropper, pipette or atomizer that delivers a predetermined volume of the composition.

Administration to the respiratory tract can be achieved by the use of an aerosol preparation in which the active ingredient is placed in a pressurized container together with a suitable delivery agent, such as CFC, trichlorofluormethane, dichlorofluormethane, carbon dioxide or other suitable gas. The dosage may be controlled by an appropriate valve-system.

The pharmaceutical composition is preferably provided in individual dosage units that contain a suitable amount of the active ingredient. The individual doses may be provided in a package, or as a kit that includes a measuring device, e.g., a device for measuring oral or injectable dosages (i.e., a measuring cup, needle, or syringe). The kit can also include, other materials such buffers, diluents, filters, and package inserts with instructions for use. A label may be present on the on the kit to indicate that the composition is used for a specific therapy, and may also indicate directions for use, such as those described above.

The compositions and methods of the present invention may also be useful in reducing the side effects of traditional chemo-radio therapies, wherein lectin is administered in conjunction with the chemo-radio therapy thereby reducing the amount of toxic dosage needed to kill cells.

The invention is described in greater detail by the following non-limiting examples.

EXAMPLE 1

Materials and Methods

Cell Culture. Nontransformed and Src transformed wild-type mouse embryonic fibroblasts (WT), homozygous null Cx43 knockout brain cells (Cx43Ko), and homozygous null Cas knockout cells (CasKo) are known in the art (Goldberg, et al. (2003) J. Biol. Chem. 278:46533-46540; Shen, et al. (2006) Cancer Res. 66:1543-1552; Alexander, et al. (2004) Cancer Res. 64:1347-1358; Patwardhan, et al. (2006) J. Biol. Chem. 281:20689-20697). LA25 cells harboring a temperature sensitive v-Src construct were grown as described (Crow, et al. (1992) Oncogne 7:999-1003). B16F10 melanoma cells were obtained from ATCC, and melan-a melanocytes were as described in the art (Estler, et al. (2008) BMC Genomics 9:478). cDNA encoding murine Pdpn was released from pCMV-Sports-pdpn (Open Biosystems #MMM1013-7513215) with EcoRI and Xba1 and inserted into the complementary sites of pEF4 to create pEF4Pdpn. B16 cells were transfected with pEF4Pdpn, empty pEF4 vector, 200 nM siRNA directed against mouse Pdpn, or 200 nM control siRNA (Dharmacon, Chicago, Ill.) with LIPOFECTAMINE 2000 (Li, et al. (2008) Cancer Sci. 99:1326-1333; Shen, et al. (2007) J. Biol. Chem. 282:18914-18921). Cells transfected with pEF4 expression vectors were selected with zeocin. Clones were not taken from any cell lines, thus minimizing potential effects of clonal variation. In some experiments, cells were treated with MAA (Sigma L8025, Sentrimed MASL) or puromycin (Sigma P8833).

Layered Culture System. A Layered Culture System was used to allow separated populations of transformed and nontransformed cells to form intercellular junctions with each other as described (Alexander, et al. (2004) supra; Goldberg, et al. (2002) J. Biol. Chem. 277:36725-26730). Briefly, ten thousand Src transformed cells were plated on porous membranes (Costar) containing 300 thousand nontransformed cells on the other side. Transformed cells and nontransformed cells were able to form intercellular junctions through the pores in the membrane; however, the membrane pore size (3 pm) is small enough to prevent cells (about 20 pm in diameter) from actually migrating to the other side of the membrane (Shen, et al. (2006) supra; Alexander, et al. (2004) supra; Goldberg, et al. (2002)supra). Transformed cells were also plated alone, directly above 300 thousand nontransformed cells, or 1 mm above 300 thousand nontransformed cells as controls. Nontransformed cells were also plated on these membranes as controls. Cells were harvested and analyzed 24 hours after plating.

Expression Microarrays. Gene expression in nontransformed, Src transformed, and contact normalized Cx43Ko cells was examined by microarray analysis with 430 2.0 Mouse Expression Array gene chips (Affymetrix) using conventional methods (Shen, et al. (2006) supra). These arrays contain approximately 45,000 probe sets which represent over 30,000 genes. Affected probe sets displayed a difference of at least 4-fold between transformed and control cells, or at least a 2-fold change with p<0.05 by t-test with n=3. Genes that were increased by Contact Normalization were also decreased by Src, but not affected by diffusible factors from nontransformed cells or contact with other transformed cells. Conversely, genes that were decreased by Contact Normalization were increased by Src, but not affected by diffusible factors from nontransformed cells or contact with other transformed cells. All comparisons were done with cells from parallel cultures to control for variability in reagents or experimental conditions. Expression analysis was performed with Vector Xpression software 4.0 (Invitrogen).

RT-PCR. RNA was purified with Tri-reagent (Sigma, St. Louis, Mo.). cDNA was synthesized from 1 µg of RNA by with PROTOSCRIPT First Strand cDNA Synthesis Kit (NEB, Ipswich, Mass.). PCR was performed with 1 µl of cDNA with forward and reverse primers specific for GAPDH (5'-TGC ATCCTG CAC CAC CAA CT-3', SEQ ID NO:1; and 5'-TGC CTG CTT CAC CAC CTT C-3', SEQ ID NO:2), hygromycin phosphotransferase (5'-CAT GGC GTG ATT TCA TAT GCG CGA-3', SEQ ID NO:3; and 5'-TCC AGA AGA AGA TGT TGG CGA CCT-3', SEQ ID NO:4), puromycin acetyltransferase (5'-ACC GAG CTG CAA GAA CTC TTC CTC-3', SEQ ID NO:5; and 5'-AGG AGG CCT TCC ATC TGT TGC T-3', SEQ ID NO:6), Pdpn (5'-ACC AAC ACA GAC GAC CAA GAC ACT-3', SEQ ID NO:7; and 5'-AAG CAT CCA CTG TGC CTT CAG TTC-3', SEQ ID NO:8), Fhll (5'-GAG AAG TTC GAC TGT CAC TAC TGC-3', SEQ ID NO:9; and 5'-CTG ATC CTG GTA AGT GAT TCC TCC-3', SEQ ID NO:10), 4930408021Rik (5'-TGT TCT CAG AGC CCA GCA TCA CTT-3', SEQ ID NO:11; and 5'-ACA TCC TCT CAG CTG OTT CCT TCA-3', SEQ ID NO:12), 1700012B09Rik (5'-CTG TGA ACC GCA TAA GAG AAT CAA GGA GG-3', SEQ ID NO:13; and 5'-TGC CTC GAG TAG TAC TTG GCT TGT-3', SEQ ID NO:14), Tmem163 (5'-ATA GAG TCT GTC ATC ATG GGC TGG-3', SEQ ID NO:15; and 5'-ACA GGC TTC CTG TCA AGC AGA GA-3', SEQ ID NO:16), Loc677224 (5'-AAC ATC CCA GAG CCT TTG ACT CCT-3', SEQ ID NO:17; and 5'-CAA AGC TGC CAT AGC TCT ATT CGG-3', SEQ ID NO:18), 1810008K04Rik (5'-AAG CCA GGA CTC TCA CAT GCA ACT-3', SEQ ID NO:19; and 5'-AGC TTT GCA GAT GGA ACG GAA CAC-3', SEQ ID NO:20), and D4bwg0951e (5'-TGG ATG GCA TCT CAG TAG GGA GCT A-3', SEQ ID NO:21; and 5'-TTG CAC ACC AGT CCC ATG CAA A-3', SEQ ID NO:22). GAPDH was amplified at 95° C. for 5 minutes, 95° C. for 30 seconds, 55° C. for 30 seconds, and 72° C. for 30 seconds for 30 cycles, followed by 72° C. for 5 minutes. Hygromycin phosphotransferase was amplified at 95° C. for 5 minutes, 95° C. for 30 seconds, and 72° C. for 1 minute for 30 cycles, followed by 72° C. for 5 minutes. The other genes were amplified at 95° C. for 5 minutes, 95° C. for 30 seconds, 60° C. for 30 seconds, and 72° C. for 30 seconds for 30 cycles, followed by 72° C. for 5 minutes.

Western Blot Analysis. Western blot analysis was performed according to conventional methods (Shen, et al. (2006) supra; Alexander, et al. (2004)Cancer Res. 64:1347-58). Protein (10 lag/lane) was resolved by SDS-PAGE, transferred to IMMOBILON-P membranes (Millipore), and incubated with antisera specific for Pdpn (Santa Cruz Biotechnology), Cas (Santa Cruz Biotechnology), active Src kinase (Cell Signaling Technology), PARP, (Cell Signaling Technology), v-Src (Upstate Biotechnology), or β-actin (Sigma). Primary antiserum was recognized by appropriate secondary antiserum conjugated to horseradish peroxidase and detected using Enhanced Chemiluminescence (Millipore). After blotting, membranes were stained with India ink to verify equal loading and transfer.

Immunofluorescence Microscopy. Cells (300,000 per dish) were cultured on 35-mm poly-D-lysine-coated glass-bottomed culture dishes (MatTek) for 24 hours. For some experiments, lectin from Maackia amurensis (Sigma L8025) was conjugated to HILYTE FLUOR TR (Anaspec) and incubated with cells for 15 minutes at 37° C. Cells were fixed with 2% paraformaldehyde, permeabilized with 0.2% TRITON X-100 in PBS (phosphate-buffered saline) for 10 minutes, washed thrice with 0.1% TWEEN 20 in PBS followed by 1% bovine serum albumin (BSA) in PBS for 30 minutes, incubated with Pdpn antiserum (1:100) overnight at 4° C., washed, and then labeled with goat anti-syrian hamster IgG conjugated to ALEXA FLUOR 488 (Molecular Probes). Cells were visualized on ZEISS AXIOVERT or PASCAL microscope systems (Li, et al. (2008) supra; Shen, et al. (2007) supra).

Cell Growth, Migration, and Toxicity Assays. Cell monolayers were scratched and incubated with MAA for 24 hours to assess cell migration by wound healing assays, which were quantitated as the number of cells that entered an area of the wound indicated as described (Shen, et al. (2006) supra; Shen, et al. (2010) supra). Alamar blue (INVITROGEN DAL1025) was added to cells 24 hours after MAA treatment, and incubated for an additional 8 hours to assay viability, which was detected by fluorescence measurements (ex/em 570/600 nm) as directed by the manufacturer (IN-VITROGEN) in a TECAN GENIOS microplate fluorescence spectrophotometer. Cells were also stained with 0.2% trypan blue and counted with a hemocytometer to evaluate cytotoxicity. To measure cell invasion, 600,000 cells were plated in 6-well cluster plates on cell culture inserts with an 8 micron pore size (Transwell-Clear, Costar) and grown for 24 hours. Cells were then released separately from the top of the membrane and the bottom of the membrane. Invasion was then quantitated as the percent of cells found on the underside of the membrane as described (Shen, et al. (2010) supra). All experiments were performed on parallel cultures to control for variations in cell culture conditions.

Affinity Precipitation. Cells were lysed in lysis buffer (20 mM Tris-Cl pH 7.4, 150 mM NaCl, 0.5% TRITON X-100, 1 mM PMSF) on ice for 30 minutes, clarified by centrifugation, diluted to 1 mg/ml in PBS supplemented with 1 mM PMSF and 10 mM MgCl2, and incubated with lectin from M. amurensis (Sigma) conjugated to agarose beads or empty beads as controls (Thermo Scientific), on ice for 3 hours. Beads were then washed four times with PBS, and eluted in of SDS-PAGE sample buffer at 95° C. for 5 minutes. Eluted protein was examined along with nonprecipitated cell lysates by western blot analysis.

In Vivo Tumorigenesis. Mice (C57BL/6) were fed with a 200 mg food pellet containing 0 or 25 mg/kg MAA once weekly, starting the day before subcutaneous inoculation with 100,000 B16 cells in 0.1 ml PBS. Tumor volumes were measured blindly by a trained physician with a single caliper daily. Mice were sacrificed 18 days after inoculation and dissected. Tumors were fixed in formalin, paraffin embedded, sectioned (5 microns), and processed for hematoxylin/eosin staining or immunohistochemistry to detect PDPN expression with 8.1.1 monoclonal antibody as described (Shen, et al. (2006) supra; Shen, et al. (2010) supra). Samples were analyzed on a ZEISS AXIOVERT microscope with AXIOVISION software as described (Shen, et al. (2006) supra; Shen, et al. (2010) supra).

Ex Vivo Effects of Dietary MAA on Cell Migration. Mice (C57BL/6) were fed with a 200 mg food pellet containing 0, 100, or 200 mg/kg MAA 1 hour before blood was taken from subclavian vein. Blood was allowed to coagulate 1 hour at room temperature and clarified by centrifugation for 10 minutes at 20,000 g to obtain serum. This serum was added to cell culture medium (DMEM+10% FBS) to a final concentration of 20%. B16 cell monolayers were scratched, washed with DMEM, and then incubated with these media, or control medium not fortified with mouse serum, for 24 hours to assess their effects on cell migration by wound healing assays, which were quantitated as the number of cells that entered an area of the wound (Shen, et al. (2006) supra; Shen, et al. (2010) supra).

EXAMPLE 2

Screening Assay for Genes Associated with Contact Normalization

Tumor cells must overcome contact normalization by adjacent nontransformed cells in their microenvironment to become malignant or metastatic (Rubin (2007) Adv. Cancer Res. 98:117-147). Using a layered culture system, identify genes involved in this process (Shen, et al. (2006) Cancer Res. 66:1543-1552; Alexander, et al. (2004) Cancer Res. 64:1347-1358) were identified. As shown in FIG. 1, Src transformed cells were incubated on a porous membrane directly over nontransformed cells. The transformed cells and nontransformed cells were able to form intercellular junctions through the pores in the membrane while being retained as separate populations. Thus, although intercellular junctions formed between the transformed and nontransformed cells, the layers were retained as distinct populations that were separately harvested. As controls, transformed cells were also incubated alone, or 1 mm over nontransformed cells to enable communication by diffusible factors but not direct contact. As has been previously reported, cellular material is not transferred between harvested cell layers (Shen, et al. (2006) supra; Alexander, et al. (2004) supra; Goldberg, et al. (2002) J. Biol. Chem. 277:36725-36730). This was verified by the retention of the Src kinase and mRNA encoding puromycin acetyltransferase in the transformed cells, and mRNA encoding hygromycin phosphotransferase in nontransformed cells.

Using AFFYMETRIX microarrays, mice genes involved in Contact Normalization were identified. About 45,000 probe sets were examined, representing over 39,000 transcripts. The expression of genes represented by 10928 probe sets, or up to about 25% of the transcriptome, was affected 2-fold or more by Src. The expression of genes represented by up to 5560 probe sets was higher in Src transformed cells than nontransformed cells, while the expression of genes represented by up to 5368 probe sets was lower. However, only 39 genes were found to be significantly affected by Contact Normalization of Src transformed cells (Table 2). The mRNA levels of several of these genes, including Pdpn, Tmem163, Fhll, and 5 ESTs were verified by RT-PCR. The expression of these genes was clearly affected by Src and reversed by contact with nontransformed cells.

TABLE 2

| Gene Symbol | Nucleotide Accession No. | Fold Change | |
|---|---|---|---|
| | | Src[a] | CN[b] |
| Genes Increased by Src and Decreased During Contact Normalization | | | |
| 1700012B09Rik[c] | NM_029306 | 115 | −3.4 |
| Pdpn[c] | NM_010329 | 93 | −4.7 |
| Tmem163[c] | NM_028135 | 58 | −5.5 |
| Smoc2 | NM_022315 | 47 | −6.6 |
| Pstpip2 | NM_013831 | 41 | −4.5 |
| Mal | NM_010762 | 30 | −5.6 |
| Lepr | NM_146146 | 28 | −4.7 |
| Elavl2 | NM_207685 | 26 | −9.9 |
| Igsf11 | NM_170599 | 26 | −5.0 |
| Mafb | NM_010658 | 14 | −6.7 |
| LOC677224[c] | XR 034093. | 13 | −3.5 |
| 4930408O21Rik[c] | NM_001040136 | 8.8 | −4.8 |
| Elmod1 | NM_177769 | 8.3 | −5.0 |
| Atpl3a4 | NM_172613 | 7.8 | −4.7 |
| Kdr | NM_010612 | 6.6 | −3.7 |
| C9 | NM_013485 | 5.4 | −4.9 |
| Genes Decreased by Src and Increased During Contact Normalization | | | |
| Fgf7 | NM_008008 | −130 | 46 |
| D10Bwg1379e | NM_001033258 | −95 | 13 |
| Sox11 | NM_009234 | −93 | 16 |
| Ccl20 | NM_016960 | −91 | 12 |
| Vcam1[d] | NM_011693 | −78* | 22* |
| | | −56* | 16* |
| | | −55* | 12* |
| Sema3e | NM_011348 | −71 | 8.3 |
| Sdpr[d] | NM_138741 | −47 | 13* |
| | | −39 | 11* |
| Epha4 | NM_007936 | −44 | 8.3 |

TABLE 2-continued

| Gene Symbol | Nucleotide Accession No. | Fold Change Src[a] | CN[b] |
|---|---|---|---|
| Ntnl | NM_008744 | −42 | 17 |
| Cabcl | NM_023341 | −32 | 5.0 |
| Spry1 | NM_011896 | −26 | 4.5 |
| Lox11 | NM_010729 | −25 | 9.9 |
| 1810008K04Rik[c] | NM_001081050 | −19 | 9.0 |
| Pdgfrb | NM_008809 | −18 | 3.9 |
| D4Bwg0951e[c] | NM_026821 | −17 | 4.2 |
| Fhl1[c,d] | NM_001077361 | −16 | 11 |
| Gpr126 | NM_001002268 | −16* | 5.7* |
|  |  | −13* | 5.7* |
| Egfr | NM_207655 | −16 | 5.2 |
| Itih2 | NM_010582 | −12 | 7.3 |
| Epb4.113 | NM_013813 | −12 | 5.6 |
| Il1rll | NM_001025602 | −9.7 | 8.3 |
| Wnt5a | NM_009524 | −9.1 | 4.6 |
| Tmem56 | NM_178936 | −8.2 | 4.4 |

[a]Expression in Src transformed cells divided by expression in nontransformed cells.
[b]Expression in transformed cells divided by expression in transformed cells undergoing Contact Normalization.
[c]Effects confirmed by RT-PCR.
[d]Genes previously shown to be induced by Contact Normalization.
*Represent results with different probe sets.

As shown in Table 2, the expression of 23 genes was suppressed by Src and increased by contact normalization. Some of these genes encode proteins that mediate events including growth factor signaling (Fgf7, Epha4, Spry1, Pdgfrb, Gpr126, Egfr, Wnt5a, and Il1r11) and transcription (Sox11 and Fhl1). Many of these genes have been implicated in the regulation of tumor cell growth and migration. For example, recent experiments indicate that Epb4.113 (erythrocyte protein band 4.1-like 3) (Cavanna, et al. (2007) J. Cell Sci. 120:606-616) and Itih2 (inter-alpha-trypsin inhibitor heavy chain) (Werbowetski-Ogilvie, et al. (2006) Cancer Res. 66:1464-1472) can suppress tumor cell invasion and metastasis. Induction of three of these genes, Vcaml, Sdpr, and Fhl1 is associated with contact normalization (Alexander, et al. (2004) supra). Interestingly, these genes are candidate biomarkers that are suppressed in malignant tumor cells (Li, et al. (2008) Cancer Sci. 99:1326-1333). For example, Src utilizes Cas to suppress Fhl1 expression in order to promote tumor cell migration (Shen, et al. (2006) supra).

The expression of 16 genes was increased by Src and suppressed by contact normalization. These genes are of great interest since they may be required for malignant growth and metastasis. These genes encode proteins that mediate events including cation (Smoc2, Atp13a4) and glutamate (Tmem163) transport, neuronal development (Mal), energy homeostasis (Lepr), mRNA transcription (Mafb) and stabilization (Elav12), cell adhesion (Igsf11), growth factor signaling (Kdr), and immunological activity (C9). Some of these gene products may act as biomarkers and targets for chemotherapy. For example, inhibitors have been generated to target kinase insert domain receptor (Kdr) in order to prevent VEGF signaling and suppress angiogenesis required for malignant tumor growth (Schenone, et al. (2007) Curr. Med. Chem. 14:2495-2516). Immunological reagents have also been targeted to immunoglobulin superfamily 11 (IGSF11) (Watanabe, et al. (2005) Cancer Sci. 96:498-506) and podoplanin (Pdpn) (Kato, et al. (2008) Cancer Sci. 99:54-61) in order to prevent tumor cell invasion and metastasis.

Since the gap junction protein Cx43 can affect transformed cell migration (Xu, et al. (2006) Development 133:3629-3639; Shao, et al. (2005) Cancer Res. 65:2705-2711), the effects of Src on Pdpn expression were analyzed in Cx43Ko (knock out) and wild-type cells. While more Pdpn was found in wild-type cells than Cx43Ko cells, western blot analysis revealed that Src augmented Pdpn protein expression in both cell types. These findings were confirmed by immunofluorescence microscopy.

These data indicate that Pdpn acts downstream of Src and Cas along the pathway leading to nonanchored tumor cell growth and migration. This study presents an example of how genes that are induced by Src and suppressed by Contact Normalization can be utilized as biomarkers and promising targets for chemotherapy. These genes also find application in assessing the role of the proteins encoded thereby in malignant growth potential.

EXAMPLE 3

Src Utilizes Cas to Induce Pdpn Expression

Pdpn expression was notably affected by Src and Contact Normalization. This was intriguing since Pdpn can promote tumor cell migration leading to malignant and metastatic growth (Wicki, et al. (2007) Br. J. Cancer 96:1-5; Kato, et al. (2008) supra; Nakazawa, et al. (2008) Blood 112(5):1730-9). It has been found that Src utilizes Cas to suppress Fhl1 expression in order to promote nonanchored cell growth and migration of Src transformed cells (Shen, et al. (2006) supra). Therefore, the effects of Src on Pdpn expression were examined in cells with and without Cas. This analysis indicated that more Pdpn was found in Src transformed cells CasKo cells transfected with Cas than control transfectants. These data indicate that Src utilizes Cas to augment Pdpn expression and promote tumor cell migration.

The effects of Pdpn on the motility of Src transformed cells were examined by transfection with siRNA. This analysis indicated that Pdpn protein expression was decreased in Src transfected cells transfected with siRNA directed against Pdpn. Wound healing assays showed that this decrease in Pdpn expression reduced the migration of Src transformed cells by over 60%. These data indicate that Src induced Pdpn expression to promote cell migration.

The effects of Pdpn on the motility of nontransformed cells were also examined by transfection with cDNA. Western blot analysis demonstrated that nontransformed cells, transfected with cDNA encoding Pdpn, expressed Pdpn protein levels comparable to Src transformed cells. Immunofluorescent microscopy found Pdpn localized to the plasma membrane where it may act as a signaling receptor. Pdpn expression did not significantly affect the growth or anchorage dependence of nontransformed cells. However, Pdpn expression did augment the ability of nontransformed cells to migrate by over 5 fold, achieving levels comparable to Src transformed cells. Thus, Pdpn did not require transforming Src activity to promote cell migration. Nonetheless, since Pdpn did not augment nonanchored growth, it was not sufficient to increase colonization of nontransformed cells.

Figure 2A:
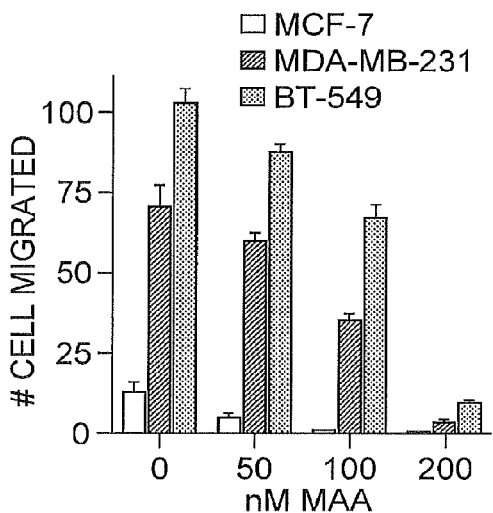
FIGS. 2A and 2B show the effect of lectins in a wound healing migration assay (FIG. 2A) and toxicity assay (FIG. 2B). Migration assays were performed on confluent monolayers of cells treated with varying concentrations of *Maackia amurensis* lectin (MAA) as indicated. Data are shown as the number of cells that migrated into a 300×300 micron area along the center of the wound in 24 hours (mean+SEM, n=7). MAA toxicity was evaluated by Trypan blue staining of cells from wound healing assays. Data are shown as thepercent of live cells from equivalent samples of each well (mean+SEM, n=4).
Figure 2B:
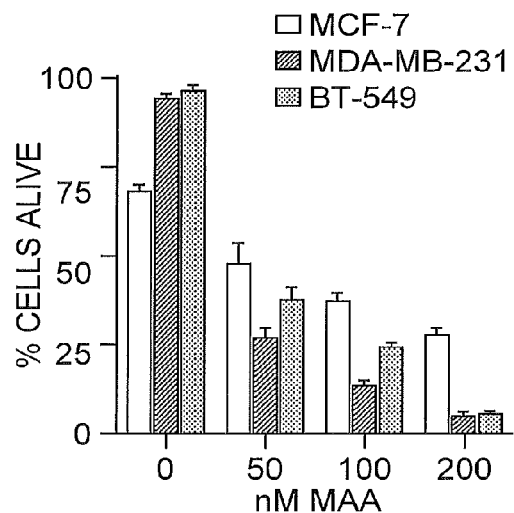

In addition to Src transformed mouse cells, Pdpn expression levels were also examined along with the migration of human mammary carcinoma cells. This analysis indicated that levels of Pdpn expression correlated well with the migration of MCF7, MDA-MB-231, BT-549 cells shown in FIG. 2. These data are consistent with Pdpn augmenting the migration of epithelial tumor cells.

EXAMPLE 4

Model Systems for Analyzing Biomarkers and Chemotherapeutic Targets

Cell systems of use in identifying biomarkers and chemotherapeutic targets to specifically detect and neutralize malignant and metastatic cancer cells that are not controlled by Contact Normalization are listed in Table 3. Using such systems it has been found that Src induces the expression of Pdpn and promotes anchorage indendence and motility required for tumor cell invasion metastasis. It has also been demonstrated that some plant lectins can bind to podoplanin and inhibit nonanchored tumor cell growth and motility at nontoxic concentrations. Therefore, natural products and compounds derived from natural products can be used in the prevention of malignant progression without harming other cells of the body.

TABLE 3

| Cells | Src | Cas | Pdpn | Anch. Independ. | Migration |
|---|---|---|---|---|---|
| CasKO (homozygous null Cas knockout cells) | | | | | |
| CasKOHP | − | − | − | − | − |
| CasKOHP-Pdpn | (−) | (−) | (+) | (+) | (+) |
| CasKOHP-Ef4 | (−) | (−) | (−) | (−) | (−) |
| CasWt | − | + | − | − | − |
| CasKOSrc | + | − | − | − | − |
| CasWtSrc | + | + | + | + | + |
| CasWtSrc-siCas | (+) | (−) | (−) | (−) | (−) |
| CasWtSrc-siPdpn | (+) | (+) | (−) | (−) | (−) |
| CasWtSrc-siCntl | (+) | (+) | (+) | (+) | (+) |
| MEF (mouse embryonic fibroblasts) | | | | | |
| Mef | − | + | − | − | − |
| Mef-Pdpn | (−) | (+) | (+) | (+) | (+) |
| Mef-Ef4 | (−) | (+) | (−) | (−) | (−) |
| MefSrc | + | + | + | + | + |
| MefSrc-siCas | (+) | (−) | (−) | (−) | (−) |
| MefSrc-siPdpn | (+) | (+) | (−) | (−) | (−) |
| MefSrc-siCntl | (+) | (+) | (+) | (+) | (+) |
| LA25 (temperature sensitive Src transformants) | | | | | |
| LA25-34 C | + | + | + | + | + |
| LA25-siCas-34 C | + | − | (−) | (−) | (−) |
| LA25-siPdpn-34 C | (+) | (+) | (−) | (−) | (−) |
| LA25-siCntl'-34 C | + | + | (+) | (+) | (+) |
| LA25-39 C | − | + | − | − | − |
| LA25Ef4-39 C | (−) | (+) | (−) | (−) | (−) |
| LA25Pdpn-39 C | (−) | (+) | (+) | (+) | (+) |

Anticipated results are shown in parentheses.

EXAMPLE 5

Targeting Podoplanin with a Plant Lectin to Inhibit Tumor Cell Growth and Migration PDPN is a transmembrane mucin glycoprotein receptor that augments tumor cell migration. PDPN expression can be induced by tumor promoters including TPA, oncogenic Ras, and Src (Nose, et al. (1990) *Cell Growth Differ.* 1:511-518; Gandarillas, et al. (1997) *Mol. Carcinog.* 20:10-18; Shen, et al. (2010) *J. Biol. Chem.* 285:9649-9656). PDPN regulates the activities of effectors including ezrin, Rho, and Cdc42 to mediate filopodia formation and promote tumor cell metastasis (Wicki & Christofori (2007) *Br. J. Cancer* 96:1-5; Martin-Villar, et al. (2009) *Int. J. Biochem. Cell. Biol.* 41:1421-29; Navarro, et al. (2010) *Am. J. Physiol. Lung Cell. Mol. Physiol.* 300(1):L32-42).

PDPN is found at the invasive front of many tumors, which is consistent with its role in promoting malignant invasion (Martin-Villar, et al. (2005) *Int. J. Cancer* 113:899-910; Wicki, et al. (2006) *Cancer Cell* 9:261-272; Wicki & Christofori (2007) supra). For example, PDPN expression is strongly induced in about 40% of breast cancers (Wicki, et al. (2006) supra; Kono, et al. (2007) *Int. J. Oncol.* 31:501-508), 50% of oral cancers (Martin-Villar, et al. (2005) supra; Yuan, et al. (2006) *Cancer* 107:563-9; Kawaguchi, et al. (2008)*J. Clin. Oncol.* 26:354-360), and 80% of skin cancers (Schacht, et al. (2005)*Am. J. Pathol.* 166:913-921; Liang, et al. (2007) *Am. J. Surg. Pathol.* 31:3014-310). The bulk of the PDPN protein, about 150 amino acids, lies outside of the cell and could serve as an ideal target to combat cancer invasion and metastasis (Wicki & Christofori (2007) supra; Kunita, et al. (2007) *Am. J. Pathol.* 170:1337-1347).

Antibodies against PDPN can inhibit lung metastasis of transformed cells that express PDPN (Nakazawa, et al. (2008) *Blood* 112(5):1730-9; Kato, et al. (2008) *Cancer Sci.* 99:54-61). However, alternatives to antibodies are needed (Johnson & Brown (2010) *Semin. Oncol.* 37:345-58). As an alternative, lectins are resistant to gastrointestinal proteolysis and can be taken orally to affect a wide range of diseases including cancer. Indeed, dietary lectins can block the action of endogenous pro-metastatic lectins (such as galectins or selectins) to inhibit tumor cell growth. However, most anti-cancer lectins that have been examined thus far target receptors that have not been identified (Pryme, et al. (2006) *Histol. Histopathol.* 21:285-99; Hasan, et al. (2007) *Cancer Lett.* 253:25-33; Pusztai, et al. (2008) *Front. Biosci* 13:1130-40; Liu, et al. (2010) *Cancer Lett.* 287:1-12).

The extracellular domain of PDPN is highly 0-glycosylated with sialic acid, α2,3 linked to galactose and has been shown to associate with lectin from the legume tree *M. Amurensis* (MAA) and promote cell migration (Scholl, et al. (1999) J. Cell Sci. 112 (Pt24):4601-13; Wicki & Christofori (2007) supra). It has now been shown that a lectin with affinity for O-linked carbohydrate chains containing sialic acid binds to PDPN to inhibit the growth and migration of melanoma cells at nanomolar concentrations. This approach demonstrates how lectins may be used as dietary agents that target specific receptors to combat malignant cell growth.

The analysis described here was carried out with Src transformed cells, which displayed strong PDPN expression and motility (Shen, et al. (2010) *J. Biol. Chem.* 285:9649-56). The results of this analysis indicated that MAA associated with PDPN on the membrane of Src transformed cells. Note that MAA did not target the membrane of cells that did not express PDPN, which, along with functional studies described herein, attests to its preferential targeting. In addition, MAA associated with PDPN in lysates from transformed cells during affinity precipitation experiments. Moreover, using human melanoma cells that express Pdpn, it was found that the growth of LOX IMVI and SK-MEL-5 cells, which express relatively high levels of Pdpn, was inhibited by greater than 85% with 325 nM or less MAA, whereas growth of UACC-257 cells, which express relatively lower levels of Pdpn, was inhibited by less than 20%.

As has been reported (Shen, et al. (2010) supra), SRC transformed cells expressed more PDPN and migrated more than nontransformed controls. Therefore, it was determined whether binding of MAA to PDPN would inhibit transformed cell migration. The MAA used in this analysis had the unique sequence: SDELSFTINN FVPNEADLLF QGEASVSSTG VLQLTRVENG QPQQYSVGRA LYAAPVRIWD NTTGSVASFS TSFTFVVKAP NPTITS- DGLA FFLAPPDSQI PSGRVSKYLG LFNNSNSDSSN- QIVAVEFDT YFGHSYDPWD PNYRHIGIDV NGIESIK- TVQ WDWINGGVAF ATITYLAPNK TLIASLVYPS NQTSFIVAAS VDLKEILPEW VRVGFSAATG YPTQVETHDV LSWSFTSTLE ANCDAATEN (SEQ ID NO:23).

This analysis indicated that MAA significantly inhibited transformed cell migration, with 385 nM, 770 nM, and 1540 nM inhibiting cell migration by over 25%, 50%, and 75%, respectively (p<0.0002 by ANOVA). In addition to inhibiting cell migration, MAA also inhibited the growth of Src transformed cells in a dose-dependent fashion (p<0.0001 ANOVA). In contrast, MAA did not inhibit the growth of nontransformed cells in an equally dose-dependent fashion (p=0.28 by ANOVA).

To verify the functional relevance of MAA targeting PDPN on cell migration, the effect of MAA (385, 770 and 1540 nM) on nontransformed cells transfected with PDPN or empty parental vector was investigated. Since PDPN expression is sufficient to promote cell migration (Scholl, et al. (1999) supra; Wicki & Christofori (2007) supra; Shen, et al. (2010) supra), nontransformed cells transfected with PDPN migrated several fold more than control transfectants. In addition, MAA reduced the migration of these nontransformed PDPN transfected cells in a dose-dependent fashion (p<0.0001 by ANOVA). For example, 385 nM MAA decreased the migration of PDPN transfectants by over 40%.

In addition to inhibiting cell migration, MAA was also toxic to PDPN expressing cells in a dose-dependent fashion (p<0.0001 ANOVA). In contrast, MAA did not inhibit the viability of empty vector transfectants in an equally dose-dependent fashion. For example, 1540 nM MAA decreased Trypan blue exclusion of PDPN transfectants by over 70%, but control transfectants by only about 30%.

Studies indicate that PDPN expression is strongly induced in about 80% of skin cancers (Schacht, et al. (2005) supra; Liang, et al. (2007) supra). Consistent with its role in tumor cell invasion and metastasis, malignant B16 melanoma cells expressed higher levels of PDPN and migrated significantly better than nontransformed Melan-a melanocytes (more than 25 cells/field vs. 2.5 cells/field). MAA effectively suppressed melanoma cell migration at concentrations of 308 nM or less. In addition, MAA inhibited melanoma cell growth in a dose-responsive manner (p<0.0001 by ANOVA). Moreover, MAA was significantly more toxic to B16 melanoma cells than Melan-a cells (p=0.0005 by ANOVA). An invasion chamber was used to further investigate the effects of MAA on melanoma cell growth and migration. While 385 nM MAA was not significantly toxic to B16 melanoma cells (p>0.2 compared to controls), invasion through 8 micron pores was decreased by over 40-fold.

To verify the effects of PDPN and MAA on melanoma cell growth and migration, siRNA was employed. This analysis showed that PDPN siRNA effectively decreased B16 Pdpn expression levels and cell migration. This decreased PDPN expression resulted in a 25% decrease to MAA toxicity. These data indicated that while PDPN may not be the only MAA target expressed by these melanoma cells, it is a functionally relevant receptor that can be targeted to prevent melanoma cell growth and migration.

Since lectins are resistant to gastrointestinal proteolysis (Pryme, et al. (2002) supra; Pusztai, et al. (2008) supra), the effects of dietary MAA on tumor cell growth in vivo were examined. Oral administration of 25 mg/kg of MAA once a week inhibited the subcutaneous growth of melanoma cells in mice by approximately 50% (p<0.05 by ANOVA). Moreover, no adverse effects on mouse health or physiology were observed over the course of these experiments based on animal behavior, weight, and organ analysis after dissection.

PDPN expression was evident in melanoma cells of tumors in vivo and was more intense in tumor cells from control animals than animals treated with MAA. In addition, tumor cells from MAA-treated animals appeared more epithelial in nature, with a relatively flattened morphology and more restricted PDPN staining than tumors from untreated animals. Interestingly, blood filled vascular spaces lined by tumor cells were much smaller and less numerous in tumors from MAA-treated mice than from control animals. Specifically, tumor vascularization was quantified as the percent of each field (0.8 mm$^2$) occupied by blood vessels it was observed that samples from MAA-treated mice had fewer than then 5% blood vessels in each field compared to 36% in control animals. Thus, like some other anticancer agents, MAA appeared to inhibit blood tumor vascularization, which may contribute to its ability to inhibit tumor growth (Rybak, et al. (2003) Cancer Res. 63:2812-2819). These experiments have been repeated with similar results.

Serum was taken from mice fed MAA and then examined for its effects on melanoma cell migration in vitro to verify that this dietary lectin can survive gastrointestinal proteolysis to remain biologically active in the circulatory system. This analysis indicated that serum from mice fed 100 or 200 mg/kg MAA inhibited melanoma cell migration by about 30% or over 80% compared to mice fed no MAA, respectively (p<0.0001 by ANOVA). These data clearly indicate that dietary administration of MAA can result in biologically relevant levels of circulating product that are sufficient to inhibit melanoma cell migration.

To demonstrate the broad applicability of MAA against different cancers, the effects of MAA on human mammary carcinoma cells was also examined. This analysis indicated that MAA was more effective on BT-549 and MDA-MB-231 cells, which expressed high levels of Pdpn, than MCF-7 cells, which expressed lower levels. The interaction between cell type and MAA exposure accounted for 18% of the variation of migration between samples (FIG. 2A) and 10% of the variation of toxicity between samples (FIG. 2B) (p<0.0001 by two-way ANOVA).

The lectin jacalin, derived from the jackfruit tree *Artocarpus integrifolia*, was used as a control in some of these studies because it preferentially binds to glycoconjugates containing galactosyl (31,3)N-acetylgalactosamine (Lehmann, et al. (2006) *Cell Mot. Life Sci.* 63:1331-1354). In contrast to MAA, jacalin does not reduce cell migration at nontoxic concentrations and appeared to augment cell migration at concentrations of up to 400 nM. Thus, suppression of tumor cell migration appeared to be lectin-specific and consistent with binding to extracellular moieties presented by Pdpn.

To further demonstrate the use of lectin in the treatment of cancer GIso values were determined using a panel of more than 50 cancer cell lines. $GI_{50}$ values represent the concentration of the anticancer agent that inhibits the growth of cancer cells by 50% (in other words, after giving the agent, there is a 50% reduction in cancer cell proliferation). This analysis indicated that MAA inhibits the growth of cancer cells including leukemia, non-small cell lung cancer, colon cancer, CNS cancer, melanoma, ovarian cancer, renal cancer, prostate cancer and breast cancer (Table 4).

TABLE 4

| Cancer | Cell Line | $GI_{50}$ |
| --- | --- | --- |
| Leukemia | CCRF-CEM | 6.56E−8 |
| | HL-60(TB) | 6.67E−8 |
| | K-562 | >7.68E−7 |
| | MOLT-4 | 5.71E−8 |
| | RPMI-8226 | >7.68E−7 |
| | SR | 8.93E−8 |

TABLE 4-continued

| Cancer | Cell Line | GI$_{50}$ |
|---|---|---|
| non-small cell lung cancer | A549/ATCC | 3.87E-7 |
| | EKVX | 3.43E-7 |
| | HOP-62 | 3.18E-7 |
| | HOP92 | 1.30E-7 |
| | NCI-H226 | >7.68E-7 |
| | NCI-H23 | >7.68E-7 |
| | NCI-H322M | >7.68E-7 |
| | NCI-H460 | 3.80E-7 |
| | NCI-522 | >7.68E-7 |
| colon cancer | COLO 205 | >7.68E-7 |
| | HCC-2998 | >7.68E-7 |
| | HCT-116 | 3.46E-7 |
| | HCT-15 | 9.47E-8 |
| | KM12 | 6.39E-7 |
| | SW-620 | >7.68E-7 |
| CNS cancer | SF-268 | 2.32E-7 |
| | SF-295 | 4.92E-7 |
| | SF-539 | 1.90E-7 |
| | SNB-19 | 4.83E-7 |
| | SNB-75 | 2.05E-7 |
| | U251 | 1.67E-7 |
| Melanoma | LOX IMVI | 1.01E-7 |
| | MALME-3M | >7.68E-7 |
| | M14 | 3.46E-7 |
| | MDA-MB-435 | 3.85E-7 |
| | SK-MEL-2 | >7.68E-7 |

TABLE 4-continued

| Cancer | Cell Line | GI$_{50}$ |
|---|---|---|
| | SK-MEL-28 | >7.68E-7 |
| | SK-MEL-5 | 2.14E-7 |
| | UACC-257 | >7.68E-7 |
| | UACC-62 | 7.29E-7 |
| ovarian cancer | IGROV1 | >7.68E-7 |
| | OVCAR-3 | >7.68E-7 |
| | OVCAR-4 | >7.68E-7 |
| | OVCAR-8 | 1.90E-7 |
| | NCI/ADR-RES | >7.68E-7 |
| | SK-OV-3 | >7.68E-7 |
| renal cancer | 786-0 | 6.03E-7 |
| | A498 | 4.38E-7 |
| | CAKI-1 | 5.16E-7 |
| | RXF 393 | 2.11E-7 |
| | SN12C | >7.68E-7 |
| | TK-10 | >7.68E-7 |
| | UO-31 | >7.68E-7 |
| prostate cancer | PC-3 | 3.06E-7 |
| | DU-145 | 4.62E-7 |
| breast cancer | MCF7 | >7.68E-7 |
| | MDA-MB-231/ATCC | 1.18E-7 |
| | HS 578T | 2.00E-7 |
| | BT-549 | 1.38E-7 |
| | T-47D | >7.68E-7 |
| | MDA-MB-468 | 1.79E-7 |

What is claimed is:

1. A chimeric molecule comprising a lectin fused to at least one heterologous polypeptide selected from the group consisting of an epitope tag, an immunoglobulin, and a combination thereof, wherein the lectin comprises SEQ ID NO:23.

2. The chimeric molecule of claim 1, wherein the lectin binds sialic acid thereby reducing tumor cell growth.

3. The chimeric molecule of claim 1, wherein the polypeptide is a polyhistidine epitope tag.

4. The chimeric molecule of claim 1, wherein the polypeptide comprises an immunoglobulin or a region thereof.

5. The chimeric molecule of claim 1, further comprising a detecting agent.

6. The chimeric molecule of claim 5, wherein the detecting agent is a fluorescent moiety.

7. A kit comprising the chimeric molecule of claim 1.

8. A method for reducing Pdpn-expressing cancer cell growth comprising administering to a subject in need thereof an effective amount of the chimeric molecule of claim 1.

9. The method of claim 8, wherein the chimeric molecule is administered orally.

10. The method of claim 8, wherein said cancer is selected from leukemia, non-small cell lung cancer, colon cancer, CNS cancer, melanoma, ovarian cancer, renal cancer, prostate cancer and breast cancer.

11. A method of targeting Pdpn expressed on a cell comprising contacting said cell with a composition comprising the chimeric molecule of claim 1.

12. A method of targeting Pdpn expressed on a cell comprising: providing a cell culture comprising tumor cells and/or normal cells; subjecting said cells to sufficient amount of an isolated lectin consisting of the amino acid sequence of SEQ ID NO: 23; allowing sufficient amount of time for said lectin to bind cellular Pdpn thereby forming a lectin-Pdpn molecular complex comprising at least a portion of the amino acid sequence set forth in the SEQ ID NO: 23 and wherein formation of said complex inhibits the activity of Pdpn.

13. The method of claim 12, further comprising identifying cells over-expressed with Pdpn by immunoassaying.

14. The method of claim 13, wherein said immunoassaying is immunofluorescence microscopy.

15. The method of claim 12, wherein said cancer is selected from leukemia, non-small cell lung cancer, colon cancer, CNS cancer, melanoma, ovarian cancer, renal cancer, prostate cancer and breast cancer.

16. A method for inhibiting cancer cell growth comprising identifying cells overexpressed with Pdpn and contacting said cells with an effective amount of lectin that binds sialic acid consisting of an amino acid sequence as set forth in SEQ ID NO: 23, thereby reducing tumor cell growth.

17. The method of claim 15, wherein said cancer is selected from skin cancer, head and neck cancer, leukemia, non-small cell lung cancer, colon cancer, CNS cancer, melanoma, ovarian cancer, renal cancer, prostate cancer and breast cancer.

18. The method of claim 15, wherein the cancer cell growth is inhibited by about 75% as compared to a cancer cell not contacted with the lectin.

19. A pharmaceutical composition comprising an isolated lectin that binds sialic acid wherein the lectin consists of the amino acid sequence as set forth in SEQ ID NO: 23 in a mixture with a pharmaceutically acceptable carrier comprising a flavor additive, a lubricant, a binder, a preservative, or an encapsulating material.

20. The pharmaceutical composition of claim 19, which is in a solid dosage form selected from powders, tablets, pills, capsules, suppositories, and dispersible granules.

21. The pharmaceutical composition of claim 20, further comprising at least two or more pharmaceutically acceptable carriers selected from a diluting agent, flavor additive, binder, and tablet-disintegrating substance.

22. The pharmaceutical composition of claim 19, which is in a liquid dosage form selected from a suspension and an emulsion.

23. The pharmaceutical composition of claim 19, further comprising one or more pharmaceutically acceptable carriers selected from an artificial coloring agent, a flavoring agent, a stabilizer, a natural or artificial sweetener, and a thickener.

24. The pharmaceutical composition of claim 19, further comprising one or more pharmaceutically acceptable carriers selected from magnesium carbonate, magnesium stearate, talc, sugar, lactose, pectin, dextrin, stiffeners, gelatins, tragacanth, methylcellulose, and sodium carboxymethylcellulose.

* * * * *